United States Patent
Wunderlich et al.

(10) Patent No.: US 9,404,785 B2
(45) Date of Patent: Aug. 2, 2016

(54) RETRACTABLE ASSEMBLY FOR IMMERSION-, FLOW- AND ATTACHMENT-MEASURING SYSTEMS

(71) Applicant: Endress + Hauser Conducta Gesellschaft für Mess- und Regeltechnik mbH + Co. KG, Gerlingen (DE)

(72) Inventors: Ingrid Wunderlich, Radebeul (DE); Thomas Pfauch, Leipzig (DE); Felix Schneider, Dresden (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 136 days.

(21) Appl. No.: 14/246,233

(22) Filed: Apr. 7, 2014

(65) Prior Publication Data

US 2014/0298901 A1    Oct. 9, 2014

(30) Foreign Application Priority Data

Apr. 8, 2013    (DE) .......................... 10 2013 103 459

(51) Int. Cl.
*G01F 15/14* (2006.01)
*C12M 1/00* (2006.01)
*C12M 1/34* (2006.01)
*G01F 3/12* (2006.01)
*G01D 11/30* (2006.01)

(52) U.S. Cl.
CPC .............. *G01F 15/14* (2013.01); *C12M 39/00* (2013.01); *C12M 41/00* (2013.01); *G01D 11/30* (2013.01); *G01F 3/12* (2013.01)

(58) Field of Classification Search
CPC ........... G01F 15/14; G01F 15/18; G01F 3/12; G01D 11/30; G01D 11/245

USPC ......................... 73/273, 272, 866.5
See application file for complete search history.

(56) References Cited

U.S. PATENT DOCUMENTS 7,272,983 B2 * 9/2007 Caderas ............... F15B 15/261
                                                            73/866.5
2011/0290045 A1 12/2011 Hanko et al.
2013/0291633 A1 11/2013 Kundscher et al.

FOREIGN PATENT DOCUMENTS

DE    EP 0545177 A1 * 6/1993 ........... G01N 27/283
DE       10241833 A1    3/2004
(Continued)

OTHER PUBLICATIONS

Feb. 25, 2014 German Search Report, German Patent Office, Munich, Germany.

*Primary Examiner* — Lisa Caputo
*Assistant Examiner* — Nathaniel T Woodward
(74) *Attorney, Agent, or Firm* — Christopher R. Powers; PatServe (57) ABSTRACT

A tool and a retractable assembly for measuring at least one measured variable of a medium in a containment, comprising: an essentially cylindrical housing; an immersion tube, which is movable axially in the housing between a service position run out from the medium and a process position run into the medium; and an engagement apparatus secured on the housing; wherein a movable piston is provided in the engagement apparatus and at least a first position and a second position of the piston are provided. The engagement apparatus holds the immersion tube in the service position when the piston is located in the first position, especially when no energy supply is present, and the engagement apparatus holds the immersion tube in an intermediate position between the service position and the process position and prevents further movement of the immersion tube in the direction of the medium when the piston is located in the second position.

15 Claims, 6 Drawing Sheets

(56) References Cited

FOREIGN PATENT DOCUMENTS

| | | |
|---|---|---|
| DE | 102010001876 A1 | 8/2011 |
| DE | 102010029029 A1 | 11/2011 |
| DE | 202012002473 U1 | 7/2012 |
| DE | 102011079348 A1 | 1/2013 |
| DE | 102012103874 A1 | 11/2013 |
| EP | 0545177 A1 | 6/1993 |
| EP | 0882896 B1 | 12/1998 |

* cited by examiner

RETRACTABLE ASSEMBLY FOR IMMERSION-, FLOW- AND ATTACHMENT-MEASURING SYSTEMS

TECHNICAL FIELD

The invention relates to a retractable assembly for immersion-, flow- and attachment-measuring systems in analytical process technology for measuring at least one measured variable of a medium in a containment. The invention relates further to a tool.

BACKGROUND DISCUSSION

Retractable assemblies are manufactured and sold by the group of firms, Endress+Hauser, in a large number of variants, for example, under the designation "Cleanfit H CPA475".

Retractable assemblies are widely used in analytical measurements technology and process automation. They serve to withdraw probes from a process, and therewith from the medium, and then to reintroduce them back into the process, without process interruption. The probes are secured in an immersion tube and by means of a manual drive or automatically, for example, pneumatically, axially moved between a process position (measuring) and a service position (maintenance, calibrating, rinsing, washing, probe exchange, etc.). These procedures take place within a certain timing cycle or as a function of other determinable or measured parameters.

Probes in the sense of this invention comprise probes with at least one receptacle for at least one sensor for measuring one or more physical or chemical, process variables.

The field of use of retractable assemblies for measuring physical or chemical process variables of a medium, e.g. a medium such as a fluid, especially a liquid, in process technology is large. Sensors are used for determining process variables, wherein the sensors can be, for example, pH-sensors, conductivity sensors, optical or electrochemical sensors for determining a concentration of a substance contained in the medium to be monitored, e.g. $O_2$, $CO_2$, certain ion types, organic compounds, and the like.

If retractable assemblies are used for accommodating a sensor for determining at least one process variable, the sensor can, in the service position, be checked, calibrated, cleaned and/or replaced, wherein the sensor is located, in such case, in the housing interior of the retractable assembly, in a so-called service chamber. In order that the medium is not contaminated by calibration-, rinse- or cleaning liquid, the service chamber is so sealed in the service position relative to the containment, in which the medium is located, that no exchange of medium/liquid can take place. Usually, there is located for this on the media-side end of the housing of the retractable assembly a seal, which, by interacting with a closure element on the immersion tube, prevents exchange of medium/liquid.

From time to time, accretions and fouling can accumulate on the closure element and/or on the mentioned seal. In order durably to prevent transfer of washing, or rinsing, medium into the containment in the service position, seal and closure element must be cleaned from time to time. This requires an open connection of the service chamber to the containment. The process is usually paused for the cleaning. It is, in such case, however, not desired that the immersion tube be located in an undefined position or even be capable of uncontrolled movement between service- and process position. In the process position, an efficient cleaning cannot be assured.

SUMMARY OF THE INVENTION

An object of the invention is to provide a controlled cleaning of the media-side seal.

The object is achieved by a retractable assembly for measuring at least one measured variable of a medium in a containment, comprising: an essentially cylindrical housing; an immersion tube, which is movable by means of an energy supply, especially pressurized air, axially in the housing between a service position run out from the medium and a process position run into the medium; and an engagement apparatus secured on the housing. A movable piston is provided in the engagement apparatus, wherein at least a first position and a second position of the piston are provided, wherein the engagement apparatus holds the immersion tube in the service position, when the piston is located in the first position and no energy supply is present, and wherein the engagement apparatus holds the immersion tube in an intermediate position between the service position and the process position and prevents further movement of the immersion tube in the direction of the medium, when the piston is located in the second position.

It can, thus, be assured that the immersion tube can be safely locked in a position between the service position and the process position—the so-called intermediate position. The engagement apparatus prevents further downwards movement, while the energy supply prevents a movement upwards. Depending on design, a further applying of the energy supply to the components can also be omitted.

"Up", "above" and related terms mean in the sense of this invention away from the medium. "Down", "below" and related terms mean in the sense of this invention toward the medium. "Outwards", "outside" and related terms mean in the sense of this invention away from the longitudinal axis of the housing. "Inwards", "within" and related terms mean in the sense of this invention toward the longitudinal axis of the housing.

In a preferred embodiment, a protrusion with a stop is provided on the immersion tube, wherein a cavity is provided at the stop, wherein the piston includes a plug, wherein in the first position of the piston the plug enters into a shape interlocking connection with the stop and holds the immersion tube in the service position, and wherein, in the second position of the piston, the plug is in the cavity and holds the immersion tube in the intermediate position and prevents further movement of the immersion tube in the direction of the medium.

It is advantageous, when the piston is rotatable about its longitudinal axis. In such case, the first position of the piston is offset from the second position by an angle, especially an angle of 90°.

The piston is, thus, rotatable and this enables movement between the first and second positions. The first position corresponds to normal operation, in which movement of the immersion tube from the service position into the process position is possible. In the first position, the engagement apparatus holds the immersion tube in the service position, especially in the case in which no energy supply is present. If the energy supply is applied, i.e. the immersion tube is to be moved downwards, the engagement apparatus must allow this. This can be made to happen, for instance, by hand or automatically, by pushing, drawing, pressing the piston outwardly, so that the path for this movement becomes free.

The piston is, thus, also movable along its longitudinal axis. In an embodiment, there is provided in the engagement apparatus an elastic element (for instance, a spring 21), which enables such movement of the piston outwardly. The piston can, in this case, also be moved outwardly, for instance, by means of auxiliary energy.

In the second position of the piston, the intermediate position of the immersion tube can be brought about. This will be explored in additional detail below.

In an advantageous form of embodiment, the stop is arranged perpendicularly to the longitudinal axis of the housing. This enables an especially safe, shape interlocking between stop and plug.

In a preferred embodiment, the plug has at least a first side and a second side, wherein the first side is embodied complementary to the stop and lies in the service position against the stop, and wherein the second side is embodied complementary to the cavity and engages in the cavity in the intermediate position.

In an advantageous variant, in such case, the plug is rectangularly shaped with a long side and a short side, wherein the long side lies against the stop in the service position, and wherein the short side engages in the cavity in the intermediate position. Especially, the long side is longer than the cavity and the short side is shorter than the cavity. It is, thus, possible that the plug blocks in the first position of the piston and in the second position enables the path for the intermediate position. Moreover, this variant enables implementing the protrusion on the immersion tube in one component.

In a preferred form of embodiment, there are provided on the media-side end of the immersion tube a closure element and on the media-side end region of the housing a seal, wherein the seal and the closure element seal the housing interior from the medium in the service position, and wherein, in the intermediate position, a connection of the housing interior to the containment is present. It is then possible to wash or rinse and to clean the media-side seal as well as the closure element.

In an advantageous embodiment, a shaped element, especially a pin, is arranged radially in the piston and protrudes at least unilaterally from the piston, wherein the engagement apparatus includes a slotted guide and the pin is constrained by the slotted guide, wherein the slotted guide is so embodied that the piston when rotated moves axially. Especially, the movement of the piston occurs inwardly along its longitudinal axis.

As already mentioned above, the piston in the first position, i.e. in normal operation, must be moved outwardly, in order that movement of the immersion tube from the service position into the process position is possible. In order that in the second position of the piston, i.e. in the position in which the intermediate position can be brought about, the piston is not pressed undesirably outwards by the immersion tube and/or the energy supply, a constrained guidance of the piston, thus the mentioned axial movement, inwards is necessary. The slotted guide is so embodied that the piston is held in this inner position.

Advantageously, movement of the piston occurs manually or automatically.

The invention relates further to a tool for a retractable assembly according to one of the above described embodiments. The tool serves for moving a piston radially to the longitudinal axis of a retractable assembly, wherein on the housing remote end of the piston a nose is provided and wherein there is provided in the tool a cavity which fits the nose.

As already mentioned, the sensor has access to the medium to be measured via an opening in the immersion tube. In such case, the opening is so embodied that, especially when the retractable assembly is applied in a pipeline, the opening is open in the flow direction, i.e. such that the sensor is optimally flowed on by the medium. In various situations, it can, however, be difficult to orient the sensor optimally.

In a further development, because of this, the immersion tube is embodied rotatably about its longitudinal axis. Then, any angle can be set.

The idea of the rotatable immersion tube described in the following paragraphs is considered to be an independent invention. Therefore, the rotatable immersion tube can be applied alone, also without the application of the engagement apparatus, the piston and the therefrom resulting opportunity for locking the immersion tube in the intermediate position. Of course, however, another option is a combination of the rotatable immersion tube with the above embodiments of the engagement apparatus.

A retractable assembly for measuring at least one measured variable of a medium in a containment and equipped with a rotatable immersion tube comprises then: an essentially cylindrical housing; an immersion tube, which is movable by means of an energy supply, especially pressurized air, axially in the housing between a service position run out from the medium and a process position run into the medium, wherein the immersion tube is rotatable about its longitudinal axis.

In an embodiment, the immersion tube is embodied in two parts with a lower, medium-contacting part and an upper part, which does not contact the medium. The lower part includes a first screw thread, especially an internal thread, while the upper part includes a second screw thread, especially an external thread.

In a form of embodiment, the upper part includes at least a first (upper) element and a second (lower) element, which are connected with one another via a roller bearing, i.e. the two elements of the upper part of the immersion tube are rotatable relative to one another. In an advantageous variant, the roller bearing is a sliding bearing or a ball bearing. Furthermore, at least one groove is formed on one of the elements, especially on the lower element.

After the immersion tube, respectively the opening of the immersion tube, is oriented in the desired direction, the upper and lower parts of the immersion tube can be screwed together, and, thus, secured in the desired position. In order to reduce this to practice, in a form of embodiment, a tool is inserted from above into the immersion tube, wherein the tool includes drivers complementary to the groove, i.e. the tool is embodied as an internal tightener. The drivers are embodied, for instance, as spheres. The tool is rotated in the immersion tube until the drivers engage in the groove. In order to facilitate this, in a form of embodiment, the drivers are pressed by a spring or by a screw outwards, i.e. away from the longitudinal axis of the tool. Through rotation of the tool, thus also the grooved element of the upper part of the immersion tube can be rotated.

This leads to the fact that the first screw thread, especially the internal thread, of the lower part of the immersion tube engages the second screw thread, especially the external thread, of the upper part of the immersion tube and, thus, the two parts are drawn together. The immersion tube is, thus, tightened, solidly connected, and secured in the desired orientation.

BRIEF DESCRIPTION OF THE DRAWINGS

The invention will now be explained in greater detail based on the appended drawing, the figures of which show as follows:

FIG. 2b is an enlarged section of the retractable assembly of FIG. 2a;

FIG. 3b is an enlarged section of the retractable assembly of FIG. 3a;

DETAILED DISCUSSION IN CONJUNCTION WITH THE DRAWINGS

In the figures, equal features are provided with equal reference characters.

Figure 1:
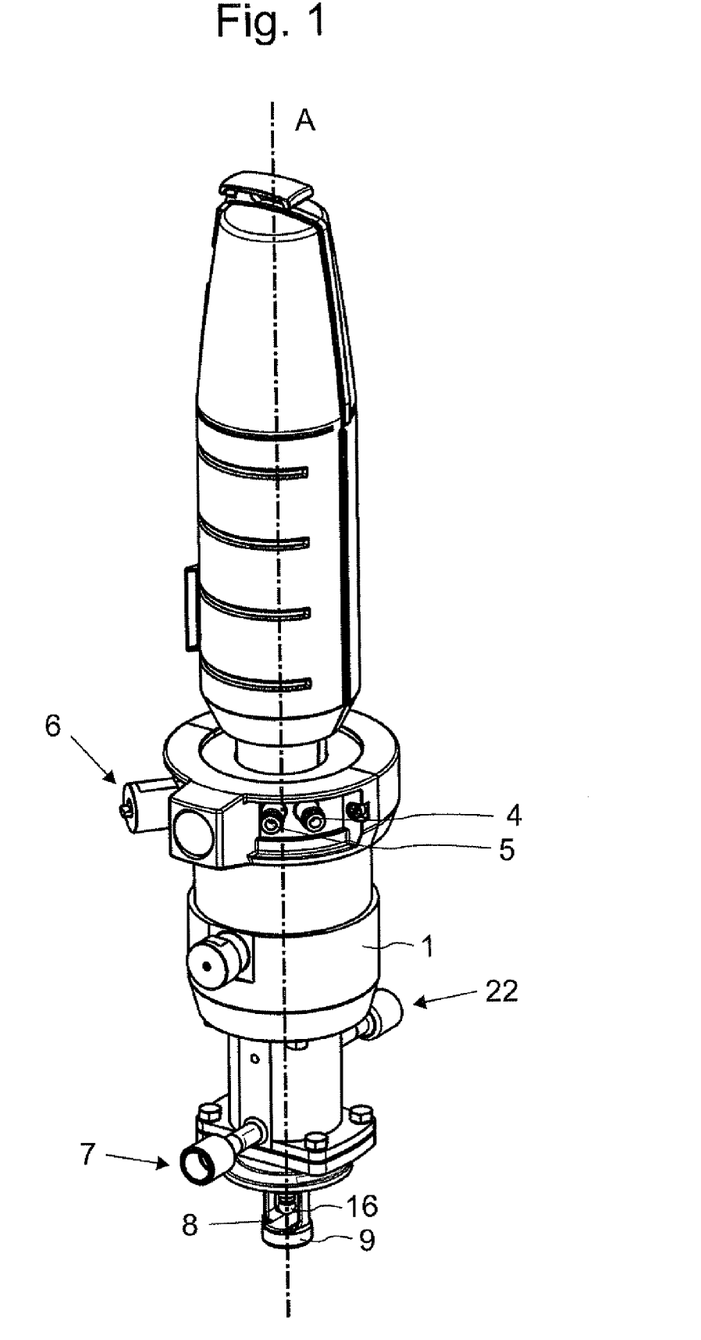
FIG. 1 is a retractable assembly of the invention with engagement apparatus in the process position.

The retractable assembly of the invention in its totality bears the reference character 1 and is shown in FIG. 1. Retractable assembly 1 is composed of an essentially cylindrical housing 2, which can be connected to a containment 11 by means of a connection means 13. The connecting means 13 can be, for instance, a flange connection, e.g. of stainless steel. Other embodiments are, however, possible. Located in the containment 11 is the medium 12 to be measured. The containment 11 can be, for instance, a container, a vat, a tube, a pipeline or the like.

FIG. 1 shows the retractable assembly 1 in the process position. This is explained in greater detail in the following.

Led within the housing 2 is an immersion tube 3. A probe is connected with the immersion tube 3 via a seating (not described in further detail), for example, via a screwed connection. The probe in the sense of the invention comprises a probe having at least one accommodation for at least one sensor 16 for measuring one or more physical or chemical, process variables. Such variables include, for example, pH-value, also via an ISFET, redox potential, absorption of electromagnetic waves in the medium, for example, waves having wavelengths in the UV-, IR-, and/or visible region, oxygen, conductivity, turbidity, concentration of metal and/or non-metal substances and temperature. Via an opening 8 in the immersion tube 3, the probe, respectively the sensor 16, has access to the medium 12 to be measured. In such case, the opening 8 is so embodied that, especially when the retractable assembly 1 is applied in a pipeline, it is open in the flow direction, i.e. such that the medium 12 can flow optimally onto the sensor 16.

The immersion tube 3 can be produced from various materials. The state of the art includes immersion tubes 3 of steel, particularly stainless steel. There are, however, applications, especially in the chemicals industry, in the case of which very resistant materials are applied. The immersion tube 3 can, thus, also be produced from a synthetic material, such as polyetheretherketone (PEEK), polytetrafluoroethylene (PTFA), a perfluoroalkoxy polymer (PFA), some other synthetic material or other resistant metals, such as, for instance, Hastelloy. The same holds for the housing 2.

The immersion tube 3 is mounted axially displaceably toward the medium 12, respectively in a direction out of the medium 12, along the central axis A. Immersion tube 3 is, thus, movable between the service position run into the housing 2 and the process position (shown in FIG. 1) run out from the housing 2. In the process position, the measuring takes place, while, in the service position, the most varied of service tasks, such as cleaning or calibration, are performed. Thus, through the connection 7, cleaning, rinse, wash and calibration liquids can be charged into the housing interior 2.1, while, through the corresponding outlet 22, which can be positioned both axially as well as also radially offset relative to the connection 7, the liquid can be drained. Also, the direction of flow of rinse, wash liquids can be reversed.

The shifting of the immersion tube 3 is effected by a manual or automatic drive, for instance, by means of an energy supply. If the energy supply is brought through the connection 4, the immersion tube 3 moves from the service into the process position. The connection 5 serves then as outlet. If the energy supply is brought through the connection 5, the immersion tube 3 moves from the process into the service position. Connection 4 then serves as outlet. Known from the state of the art are, for example, pneumatic, hydraulic and electrical drives. Although in FIG. 1 the connections 4, 5 are arranged next to one another, in the following, the terms "upper connection 4" and "lower connection 5" will be used as a convenience for distinguishing the two connections.

If the immersion tube 3 is in the service position, a portion of the immersion tube 3, especially the sensor 16, is located in the housing interior 2.1, in the so-called service chamber, for the rinsing, washing, cleaning, calibrating, etc. Located on the lower end of the immersion tube 3 is the closure element 9 for sealing off from the process. Closure element 9 seals the housing interior 2.1 from the process, and, therewith, from the medium 12. The medium 12 can be hot, poisonous, corrosive or in some other manner damaging for humans and the environment. It is, consequently, necessary to assure that the closure element 9 safely and durably seals. For such purpose, various sealing systems are installed on the housing 2. Especially, one more seals 10 are used.

Closure element 9 is provided with the already mentioned opening 8, so that the probe, respectively the sensor 16, has access to the medium 12 to be measured. In such case, the opening 8 is so embodied that, especially when the retractable assembly 1 is applied in a pipeline, it is open in the flow direction, i.e. such that the sensor 16 is optimally flowed on by the medium 12.

Figure 2A:
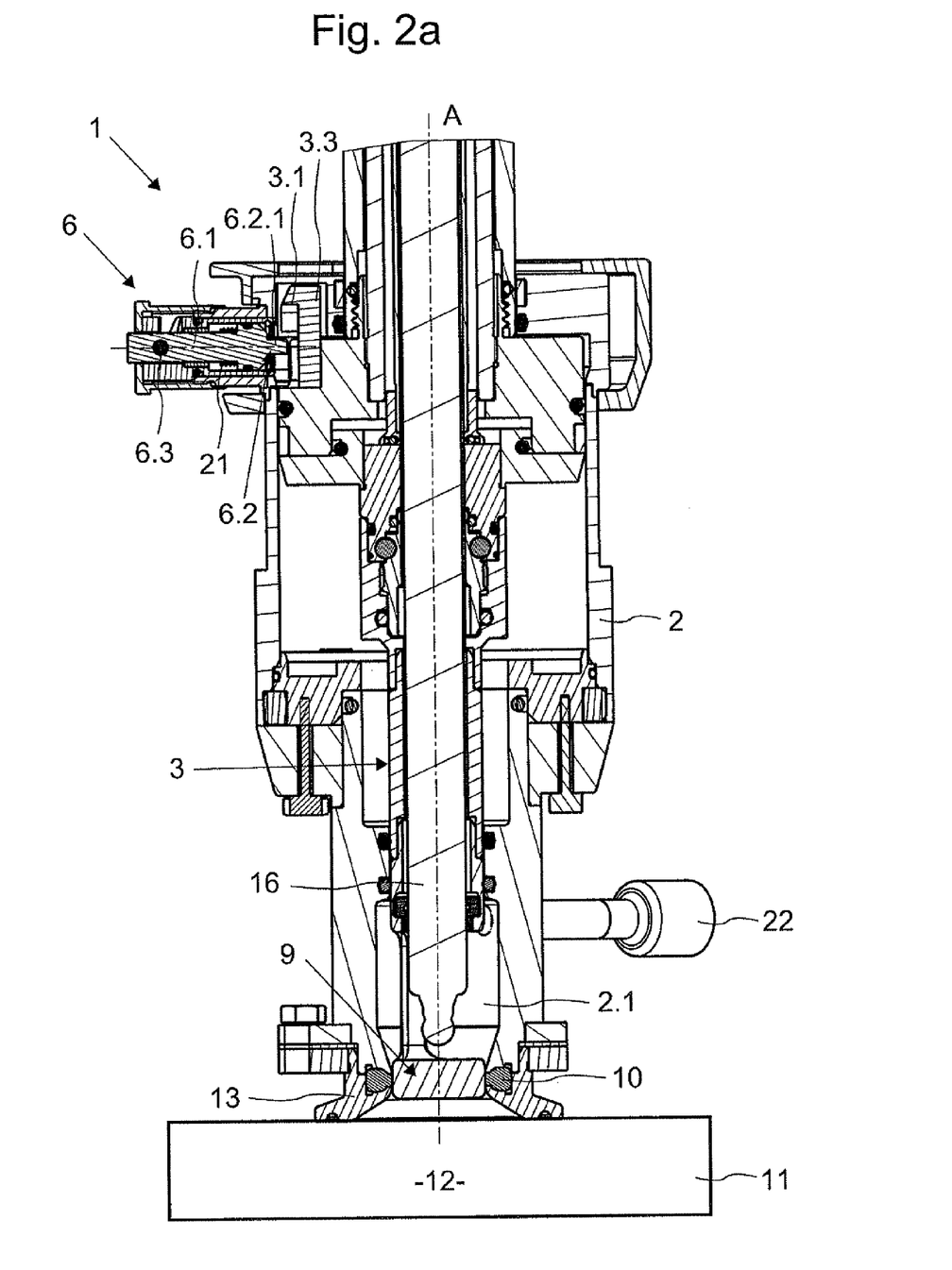
FIG. 2a is a retractable assembly of the invention in cross section in the service position.

FIG. 2a shows the retractable assembly 1 in cross section in the service position, i.e. the housing interior 2.1 is sealed from the containment 11. In order that the immersion tube 3 remains in the service position and no unintended movement in the direction of the medium 12 occurs, an engagement apparatus 6 holds the immersion tube 3 up.

As already mentioned, the terms "up", "above" and related terms mean in the sense of this invention away from the medium 12. "Down", "below" and related terms mean in the sense of this invention toward the medium. "Outwards", "outside" and related terms mean in the sense of this invention away from the longitudinal axis A. "Inwards", "Within" and related terms mean in the sense of this invention toward the longitudinal axis A.

Movably mounted in the engagement apparatus 6 is a piston 6.1. Piston 6.1 is especially rotatable about its longitudinal axis. Piston 6.1 includes on its housing end a plug 6.2 and on its housing remote end a nose 6.4. Plug 6.2 forms with a stop 3.1 of a protrusion 3.3 on the immersion tube 3 a shape interlocking, which prevents movement of the immersion tube 3 in the direction of the medium 12. See, in this connection, FIG. 2b. The stop 3.1 can, in such case, be arranged perpendicularly to the longitudinal axis A of the housing.

The first position of the piston 6.1 is the normal position. In this position, the immersion tube 3 can be run from the service position into the process position. This will now be explained in the following.

Figure 2B:
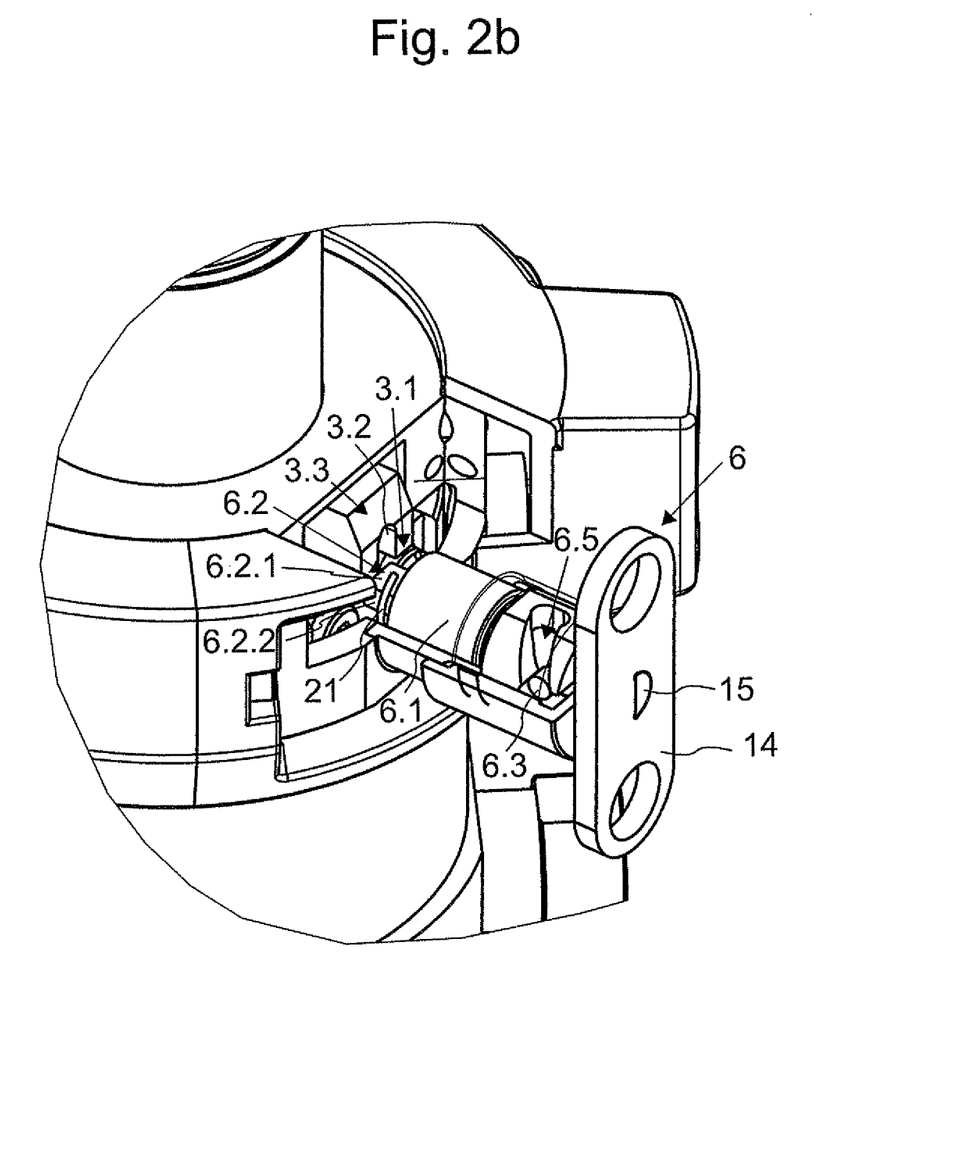

If the piston 6.1 is located in the first position, which is shown in FIG. 2a and FIG. 2b, and energy supply is introduced through the upper connection 4, the energy supply first moves the piston 6.1 outwardly. Then the immersion tube 3 moves downwards past the outwardly pushed piston 6.1 and into the process position. This is known, for instance, from the as yet unpublished patent application DE 10 2012 103 874 (US 2013291633). Alternatively, a manual or automatic shifting of the piston 6.1 outwardly can occur. Located in the engagement apparatus 6 is an elastic element, such as a spring 21, which enables such a movement of the piston 6.1.

As another alternative, it can be omitted that the immersion tube 3 is held in the service position by the engagement apparatus 6. Instead, the immersion tube 3 is held durably above, for instance, by a continuous supply of energy.

Figure 3A:
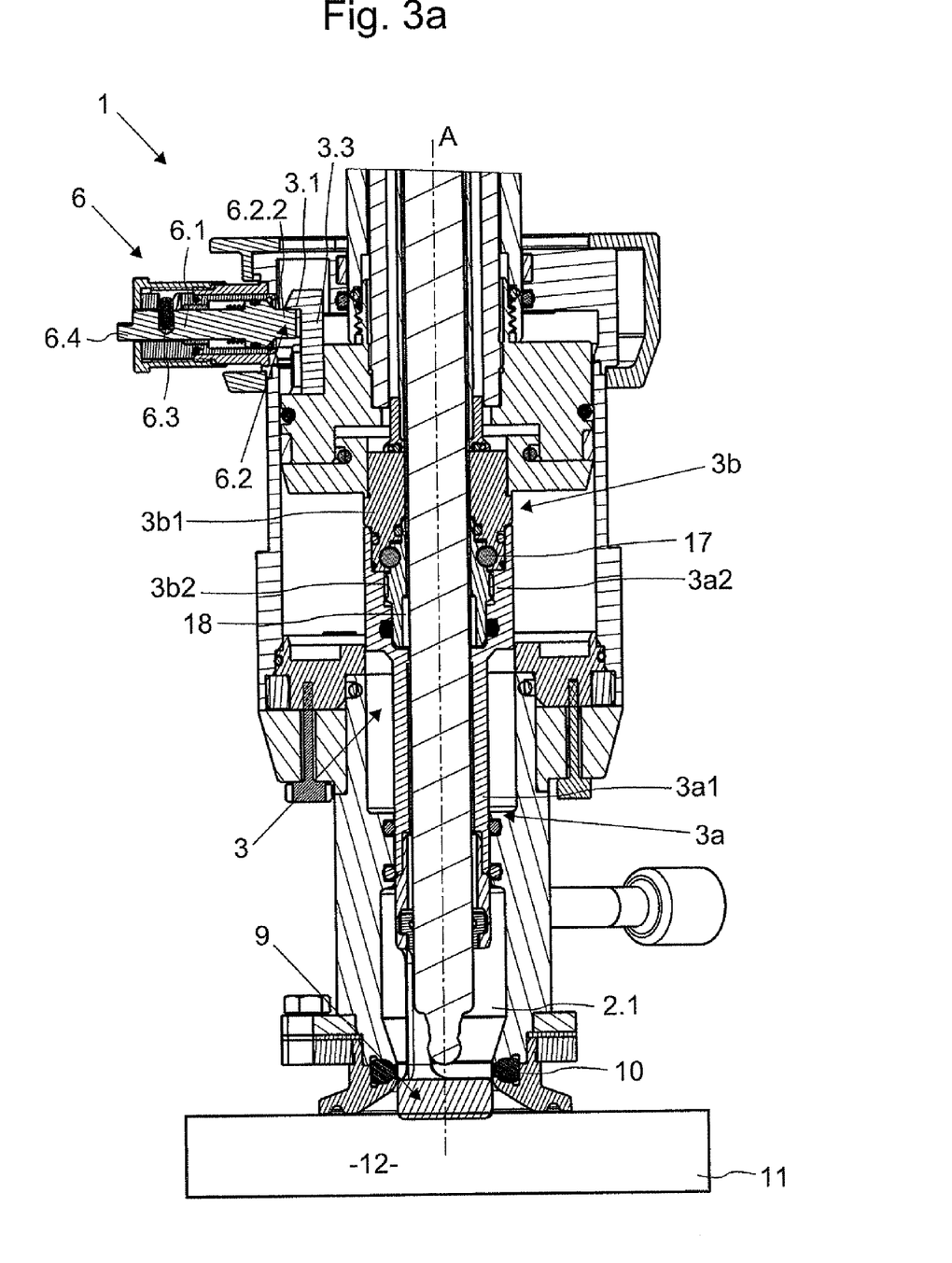
FIG. 3a is a retractable assembly of the invention in cross section in the intermediate position.
Figure 3B:
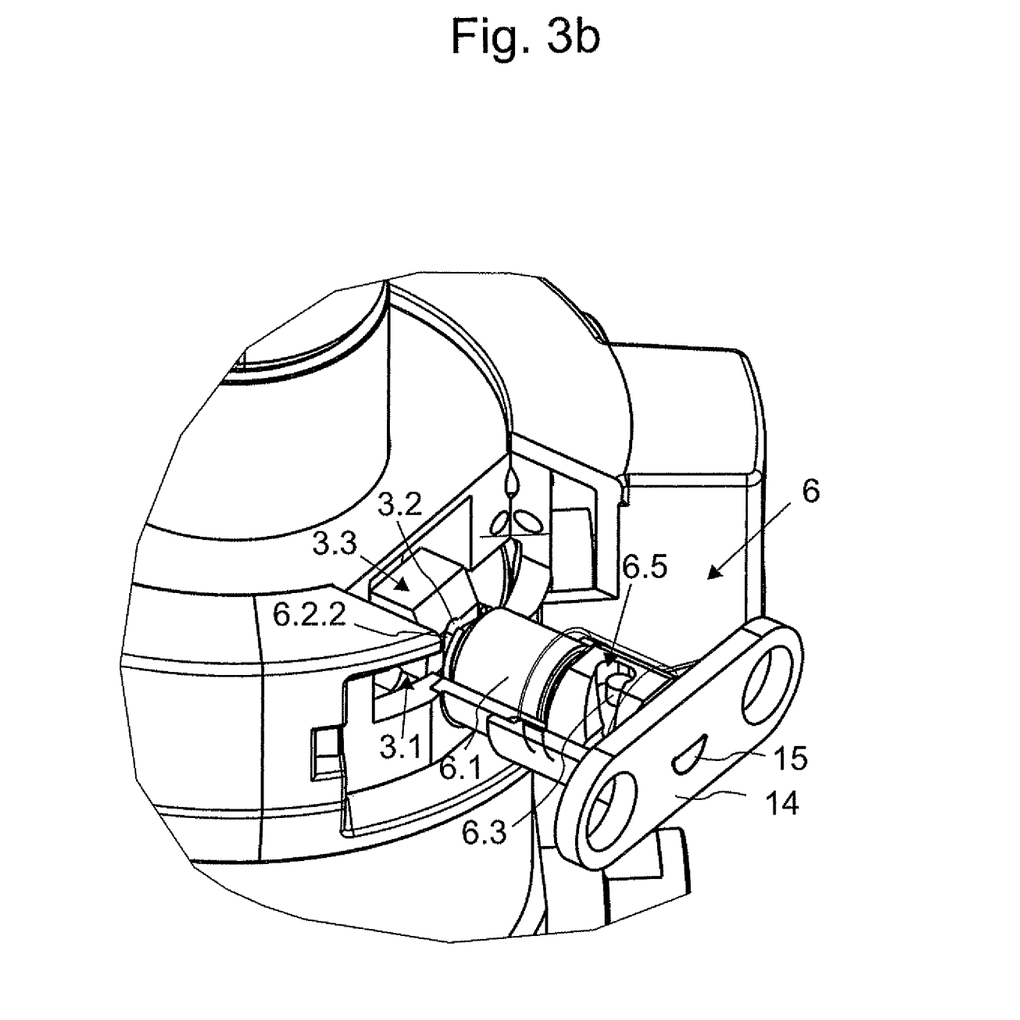

FIG. 3a and FIG. 3b show the situation when the piston is located in a second position. The second position is rotated from the first position by an angle, especially by 90°.

Along with a rotation of the piston 6.1, movement of the piston in the axial direction occurs, i.e. radially toward the housing 2. This is accomplished by a shaped element 6.3, for instance, a pin, especially a cylindrical pin, located in the piston 6.1. The shaped element 6.3 is so led in a slotted guide 6.5 that in the case of a rotation of the piston 6.1 simultaneously a translational movement takes place inwardly. The slotted guide 6.5 can, in such case, be milled into the engagement apparatus 6, or be present as a separate component in the engagement apparatus 6. An axial movement of the piston 6.1 is necessary, in order that the applied energy supply not press the piston 6.1 back outwards and, thus, allow movement of the immersion tube 3 into the process position (compare above: Mechanism for moving the immersion tube 3 from the service position into the process position). The slotted guide 6.5 prevents this; the immersion tube 3 moves only to the intermediate position.

Figure 4A:
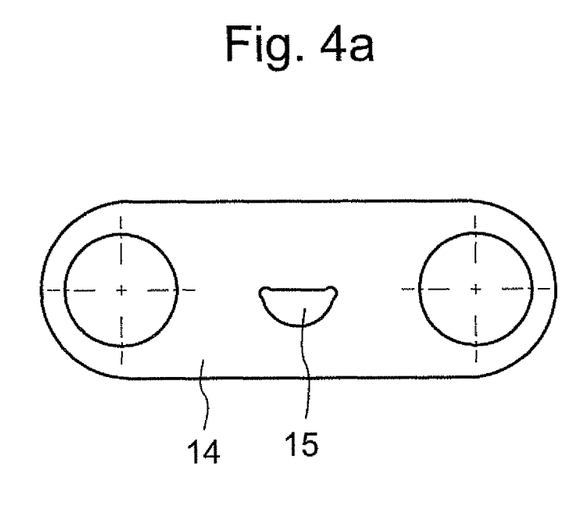
FIG. 4a is a tool of the invention for moving a piston radially to the longitudinal axis of a retractable assembly of the invention.

A rotation of the piston 6.1 is accomplished by the tool 14, which is shown in FIG. 5a. The cavity 15 fits the nose 6.4 of the piston 6.1 and enables an easy and safe adjusting of the piston 6.1. It can, in such case, involve, for instance, a D-shaped cutout. Alternatively, a rotation of the piston 6.1 can also occur by automatic means.

In FIG. 3a, one can detect the rotation of the piston 6.1 by the—compared with FIG. 2a—changed positions of the shaped element 6.3 and the plug 6.2. Plug 6.2 has at least a first side 6.2.1 and a second side 6.2.2. The first side 6.2.1 is embodied to be complementary to the stop 3.1, so that, in the service position (compare FIG. 2a and FIG. 2b), movement of the immersion tube 3 is not possible, since first side 6.2.1 and stop 3.1 shape-interlock, i.e. the shapes of the first side 6.2.1 and stop 3.1 interlock with one another.

Plug 6.2 has, for instance, a rectangular cross section with a long side and a short side. The long side corresponds, in such case, to the first side 6.2.1, i.e. the long side is against the stop 3.1 in the service position. The short side corresponds to the second side 6.2.2, i.e. the short side engages in the intermediate position in a cavity 3.2 of the protrusion 3.3. The first side 6.2.1 is, in such case, longer than the cavity 3.2, while the second side 6.2.2 is shorter than the cavity 3.2. In order that a rotation of the piston 3.1 is possible, in the intermediate position, some space is left between the upper edge of the first side 6.2.1 and the lower edge of the stop 3.1. The immersion tube 3 has, thus, some play, however, only a limited amount, so that a sealing of the housing interior 2.1 from the containment 11 is still assured.

Upon rotation of the piston 6.1, the cavity 3.2 leads to release of the shape interlocking of the stop 3.1 and the first side 6.2.1. If now energy supply is introduced through the upper connection 4, the second side 6.2.2 can travel past the stop 3.1 until it engages in the cavity 3.2. The second side 6.2.2 forms, thus, a shape interlocking with the (upper edge of the) cavity 3.2. The immersion tube 3 is, thus, locked in an intermediate position between the service position and the process position, since the energy supply prevents movement upwardly and the cavity 3.2 prevents further movement downwards. With corresponding design of the components, further applying of the energy supply can be omitted.

Since the cavity 3.2 extends essentially in the direction of the longitudinal axis A and the upper edge of the cavity 3.2 is located above the stop 3.1, the immersion tube 3 can travel further downwards by exactly this amount. This amount suffices to cancel the sealing action of seal 10 and closure element 9, since now the closure element 9 is located below the seal 10. Through the rinse, wash connection 7, inflowing washing, or rinsing, medium rinses, washes, thus cleans, the seal 10 and/or the closure element 9.

In order to rinse, wash, the seal 10 and/or the closure element 9, thus, steps are required as follows: Rotation of the piston 6.1 into the second position (manually or automatically, possibly with tool 14), charging of the upper connection 4 with energy supply, waiting until immersion tube 3 is located in the intermediate position (plug 6.2 with second side 6.2.2 is located in cavity 3.2), rinsing, washing, the housing interior 2.1 through the rinse, wash connection 7 (rinsing, washing, liquid flows into the containment 11). Most often, it is advantageous to interrupt the process, thus the medium 12, during this cleaning phase. In order to return to the service position, the above steps are executed in reverse sequence (energy supply must then be introduced from the lower connection 5).

As already mentioned, the sensor 16 has access to the medium 12 via an opening 8 in the immersion tube 3. For optimal measuring, the sensor 16 should be directly flowed on by the medium 12, i.e. the opening 8 should point in the flow direction. Frequently, the closure element 9 is cage-like, i.e. it has positions of the immersion tube 3, in which the opening 8 is not oriented in the flow direction.

Because of this, the immersion tube 3 is embodied such that it is rotatable about its longitudinal axis. FIG. 3a shows this rotatable immersion tube 3. In such case, the immersion tube 3 is embodied in two parts, with a lower, medium-contacting part 3a and an upper part 3b, which does not contact the medium.

Upper part 3a and lower part 3b of the immersion tube 3 can be produced from different materials. Especially, the lower part 3a must be resistant to the medium 12.

The lower part 3a includes besides the closure element 9, an intermediate element 3a1 and a first threaded element 3a2. The threaded element 3a has a first screw thread, for instance, an internal thread, i.e. the screw thread faces toward the longitudinal axis A. The lower part 3a of the immersion tube 3 is embodied as a single part. Thus, the described individual parts (closure element 8, intermediate piece 3a1, threaded element 3a2) are, for instance, connected with one another by welding and shown in FIG. 3a as a single part.

The upper part 3b of the immersion tube includes a top element 3b1 as well as a second threaded element 3b2. The threaded element 3b2 has a second screw thread, for instance, an external thread, i.e. the screw thread faces away from the longitudinal axis A. Formed on the threaded element 3*b*2 internally on its lower end is a groove 18. The top element 3*b*1 is connected with the threaded element 3*b*2 via a roller bearing 17, for instance, a sliding bearing or ball bearing. The threaded element 3*b*2 can, thus, turn on the top element 3*b*1. Shown in FIG. 3 are, in the fact, two rollers, the top element 3*b*1 forms the outer ring, and the threaded element 3*b*2 the inner ring, of the roller bearing 17.

Figure 4B:
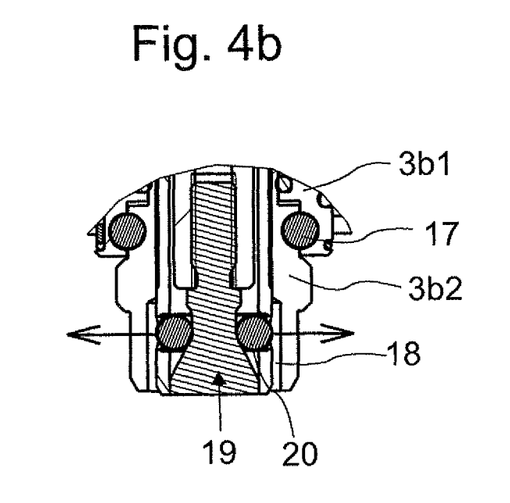
FIG. 4b is a detail view of a tool for rotationing the installed immersion tube.

For orientation of the immersion tube 3, respectively the opening 8, the screw thread is loosened, i.e. lower part 3*a* and upper part 3*b* are disassembled. First, the two parts 3*a*, 3*b* are oriented, especially, the lower part 3*a* is so turned that the opening 8 points in the flow direction. Any angle can be set. Then, with the aid of a second tool 19 (see section thereof in FIG. 4*b* showing the installed situation in the immersion tube 3) the immersion tube 3 can be secured. The tool includes drivers 20 complementary to groove 18 and is embodied as an internal tightener. The drivers 20 are embodied, for instance, as spheres.

The tool 19 is inserted into the immersion tube 3 so far from above until the driver 20 is at the height of the groove 18. Provided in the tool 19 is a spring or a screw, which presses the drivers 20 outwardly, i.e. away from the longitudinal axis. The drivers 20 push now outwardly and the tool is then rotated until the drivers 20 engage with the groove 18. Since the threaded element 3*b*2 is connected by means of roller bearing 17 with the top element 3*b*1, upon engaging of the drivers 20 with the groove 18, the threaded element 3*b*2 rotates with the rotation of the tool 19.

In this way, the second threaded element 3*b*2 rotates into the first threaded element 3*a*2. This accomplishes that the lower part 3*a* grips the upper part 3*b* of the immersion tube 3, tightens and, thus, solidly connects. The immersion tube 3 is, thus, oriented in the housing 2 with the desired orientation of the opening 8.

The invention claimed is:

1. A retractable assembly for immersion-, flow- and attachment-measuring systems in analytical process technology for measuring at least one measured variable of a medium in a containment, comprising:
   a cylindrical housing;
   an immersion tube, which is movable by means of an energy supply, axially in said housing between a service position run out from the medium and a process position run into the medium; and
   an engagement apparatus secured on said housing, wherein:
   a movable piston is provided in said engagement apparatus;
   at least a first position and a second position of said piston are provided;
   said engagement apparatus holds said immersion tube in said service position when said piston is located in said first position; and
   said engagement apparatus holds said immersion tube in an intermediate position between said service position and said process position and prevents further movement of said immersion tube in the direction of the medium when said piston is located in said second position.

2. A retractable assembly as claimed in claim 1, wherein:
   a protrusion with a stop is provided on said immersion tube;
   a cavity is provided at said stop;
   said piston includes a plug;
   in said first position of said piston said plug enters into a shape interlocking connection with said stop and holds said immersion tube in the service position; and
   in said second position of said piston the plug is in said cavity and holds said immersion tube in the intermediate position and prevents further movement of said immersion tube in the direction of the medium.

3. The retractable assembly as claimed in claim 2, wherein:
   said stop is arranged perpendicularly to the longitudinal axis of said housing.

4. The retractable assembly as claimed in claim 2, wherein:
   said plug has at least a first side and a second side;
   said first side is embodied complementary to said stop and in said service position lies against said stop; and
   said second side is embodied complementary to said cavity and engages in said cavity in said intermediate position.

5. The retractable assembly as claimed in claim 4, wherein:
   said plug is rectangularly shaped with a long side and a short side;
   said long side lies against said stop in said service position; and
   said short side engages in said cavity in said intermediate position.

6. The retractable assembly as claimed in claim 1, wherein:
   said piston is rotatable about its longitudinal axis.

7. The retractable assembly as claimed in claim 6, wherein:
   said first position of said piston is offset from said second position by an angle about its longitudinal axis.

8. The retractable assembly as claimed in claim 7, wherein:
   said first position of said piston is offset from said second position by an angle of 90°.

9. The retractable assembly as claimed in claim 6, wherein:
   a shaped element is arranged radially in said piston and protrudes at least unilaterally from said piston
   said engagement apparatus includes a slotted guide and the shaped element is constrained by said slotted guide; and
   said slotted guide is so embodied that said piston when rotated moves axially.

10. The retractable assembly as claimed in claim 9, wherein:
    said shaped element is a pin.

11. The retractable assembly as claimed in claim 1, wherein:
    a closure element is provided on a media-side end of said immersion tube;
    a seal is provided on the media-side end region of said housing;
    said seal and said closure element seal said housing interior from the medium in said service position; and
    in said intermediate position, a connection of said housing interior to the containment is present.

12. The retractable assembly as claimed in claim 1, wherein:
    movement of said piston occurs manually or automatically.

13. A tool for moving the piston radially to the longitudinal axis of a retractable assembly as claimed in claim 1, wherein:
    on a housing-remote end of said piston a nose is provided; and
    there is provided in the tool a cavity, which fits said nose.

14. The retractable assembly as claimed in claim 1, wherein:
    said energy supply is pressurized air.

15. The retractable assembly as claimed in claim 1, wherein:
    said engagement apparatus holds said immersion tube in said service position when said piston is located in said first position when no energy supply is present.

* * * * *